(12) United States Patent
Lan et al.

(10) Patent No.: US 12,280,183 B2
(45) Date of Patent: Apr. 22, 2025

(54) BULB LAMP

(71) Applicant: Shenzhen Guanke Technologies Co., Ltd, Shenzhen (CN)

(72) Inventors: Qing Lan, Shenzhen (CN); Ligen Liu, Shenzhen (CN); Liang Wu, Shenzhen (CN); Xuren Qiu, Shenzhen (CN); Qinwan Gong, Shenzhen (CN)

(73) Assignee: Shenzhen Guanke Technologies Co., Ltd, Shenzhen (CN)

( * ) Notice: Subject to any disclaimer, the term of this patent is extended or adjusted under 35 U.S.C. 154(b) by 117 days.

(21) Appl. No.: 18/295,485

(22) Filed: Apr. 4, 2023

(65) Prior Publication Data
US 2024/0216568 A1 Jul. 4, 2024

(30) Foreign Application Priority Data
Dec. 29, 2022 (CN) .................. 202223599541.X

(51) Int. Cl.
*F21K 9/238* (2016.01)
*A61L 9/20* (2006.01)
(Continued)

(52) U.S. Cl.
CPC ................ *A61L 9/20* (2013.01); *F21K 9/232* (2016.08); *F21K 9/238* (2016.08);
(Continued)

(58) Field of Classification Search
CPC . Y02A 50/20; F21K 33/0088; F21V 33/0064; F21V 29/74; F21V 7/043; F21V 33/0076; F21V 33/0096; F24F 8/22; F24F 8/20; F24F 1/0047; F24F 2221/14; F24F 2221/02; F24F 13/078; F24F 7/003; F24F 7/007; F24F 2013/205; A61L 9/20; A61L 2/10; A61L 2/0047; A61L 2209/12; A61L 9/122; F21Y 2115/10; F21Y 2103/10; F21Y 2105/10; F21Y 2107/90; F21Y 2107/00; F21Y 2113/13; F21Y 2113/30; F21K 9/27; F21K 9/232; F21K 9/66; F21K 9/238; F21K 9/278
See application file for complete search history.

(56) References Cited

U.S. PATENT DOCUMENTS

| | | | | |
|---|---|---|---|---|
| 6,621,716 B2 * | 9/2003 | Edwards | ............... | H01L 33/483 362/249.02 |
| 10,921,004 B1 * | 2/2021 | Maa | .................... | B01D 46/0005 |
| 11,160,897 B1 * | 11/2021 | Shalvi | ................. | F21V 33/0064 |

\* cited by examiner

*Primary Examiner* — Omar Rojas Cadima
(74) *Attorney, Agent, or Firm* — Maier & Maier, PLLC

(57) ABSTRACT

A bulb lamp, including a lamp shell, a light-transmitting cover, a power panel, a lamp panel, at least one illumination module and at least one sterilization module. An annular first step extends inside the peripheral side of the lamp shell, and a plurality of air inlets are provided above the first step; the light-transmitting cover is connected to the bottom ring side of the lamp shell and surrounds the lamp shell to form an accommodating cavity, the bottom of the light-transmitting cover is provided with at least one air outlet in communication with the accommodating cavity, and the accommodating cavity is in communication with the air inlet; the power panel is arranged in the accommodating cavity; the lamp panel is arranged in the accommodating cavity and is lower than the first step, and an installation space is formed between the lamp panel and the first step.

10 Claims, 10 Drawing Sheets

(51) Int. Cl.
 *F21K 9/232* (2016.01)
 *F21Y 105/18* (2016.01)
 *F21Y 115/10* (2016.01)
(52) U.S. Cl.
 CPC ....... *A61L 2209/12* (2013.01); *F21Y 2105/18* (2016.08); *F21Y 2115/10* (2016.08)

BULB LAMP

TECHNICAL FIELD

The present disclosure relates to the technical field of lamps, and in particular to a bulb lamp.

BACKGROUND

A conventional bulb lamp is generally composed of a transparent glass bulb and a tungsten filament provided in the transparent glass bulb, so that luminous illumination is performed by energizing the tungsten filament. However, when the voltage is unstable, the tungsten wire is easily blown. For this reason, more new bulb lamps change the internal tungsten filament to a LED bulb. However, the new bulb lamp, although able to reduce the possibility of burning out to a certain extent, usually has only a lighting effect in use, resulting in a single use function of the bulb lamp.

SUMMARY

The main object of the present disclosure is to provide a bulb lamp, aiming at diversifying the use functions of the bulb lamp so as to better meet people's needs.

In order to achieve the above object, the present disclosure proposes a bulb lamp comprising:
- a lamp shell, wherein an annular first step extends inside the circumferential side of the lamp shell, and a plurality of air inlets are provided above the first step;
- a light-transmitting cover, wherein the light-transmitting cover is connected to the bottom ring side of the lamp shell and encloses with the lamp shell to form an accommodating cavity, the bottom of the light-transmitting cover is provided with at least one air outlet in communication with the accommodating cavity, and the accommodating cavity is in communication with the air inlet;
- a power panel, wherein the power panel is arranged in the accommodating cavity;
- a lamp panel, wherein the lamp panel is provided in the accommodating cavity and is arranged below the first step, an installation space is formed between the lamp panel and the first step, the lamp panel is electrically connected to the power panel, and the upper surface and the lower surface of the lamp panel are both provided with at least one circuit;
- at least one illumination module, wherein the illumination module is provided on the lower surface of the lamp panel and is electrically connected to the circuit on the lower surface of the lamp panel; and
- at least one sterilization module set in the installation space and electrically connected to the circuit of the upper surface of the lamp panel.

Other features and corresponding advantages of the present application are set forth in a later portion of the specification.

The technical problem solving idea and the relevant product design scheme of the present application are: by providing at least one illumination module in the accommodating cavity formed by the lamp shell and the light-transmitting cover being enclosed, the illumination module can emit light and illuminate towards the outside through the light-transmitting cover after being powered on by the lamp panel and the power panel, so as to realize the basic function of the bulb lamp. Furthermore, at least one sterilization module is also provided in the accommodating cavity, and at the same time, at least one air inlet communicating with the accommodating cavity is provided at the peripheral side of the lamp shell, and at least one air outlet communicating with the accommodating cavity is provided at the bottom of the light-transmitting cover, so that the external air flow can enter the accommodating cavity from the air inlet, and is discharged from the air outlet to the outside after being sterilized and purified by the sterilization module, thereby achieving the function of sterilizing and purifying air. Therefore, the bulb lamp in the present solution further has an additional function of sterilizing and purifying the air based on the basic function of illuminating the outside. This makes the use function of the bulb lamp more diversified, so that people's needs can be better met.

Furthermore, the air inlet from the peripheral side of the lamp shell and the air outlet from the bottom of the light-transmitting cover makes it possible for the bulb lamp to better discharge the sterilized air down into the environment where people are located. At the same time, with this arrangement, it is also possible to better drive the unpurified gas in the lower layer to the upper layer so as to enter the bulb lamp from the peripheral side of the lamp shell for the sterilization and purification work.

Furthermore, it is particularly important that the bulb lamp in the present solution is further provided with at least one circuit on both the upper surface and the lower surface of the lamp panel, so that the illumination module and the sterilization module can be respectively provided on the lower surface and the upper surface of the lamp panel. This enables the illumination module and the sterilization module to improve the compactness of the structural distribution by sharing one lamp panel, thereby facilitating the adaptive installation of many devices, such as the illumination module and the sterilization module, in the very limited space in the bulb lamp. Furthermore, the installation space for arranging the sterilization module is formed between the first step and the lamp panel, and the installation space provides a space for the sterilization module to be vertically inserted into the lamp panel, so that the sterilization module can emit light horizontally towards the centre of the accommodating cavity so as to maximally sterilize the incoming air, and at the same time, the first step can also block the starting point of the ultraviolet rays emitted by the sterilization module, so as to reduce the possibility of the ultraviolet rays emitted by the sterilization module being emitted to the outside.

Figure 1:
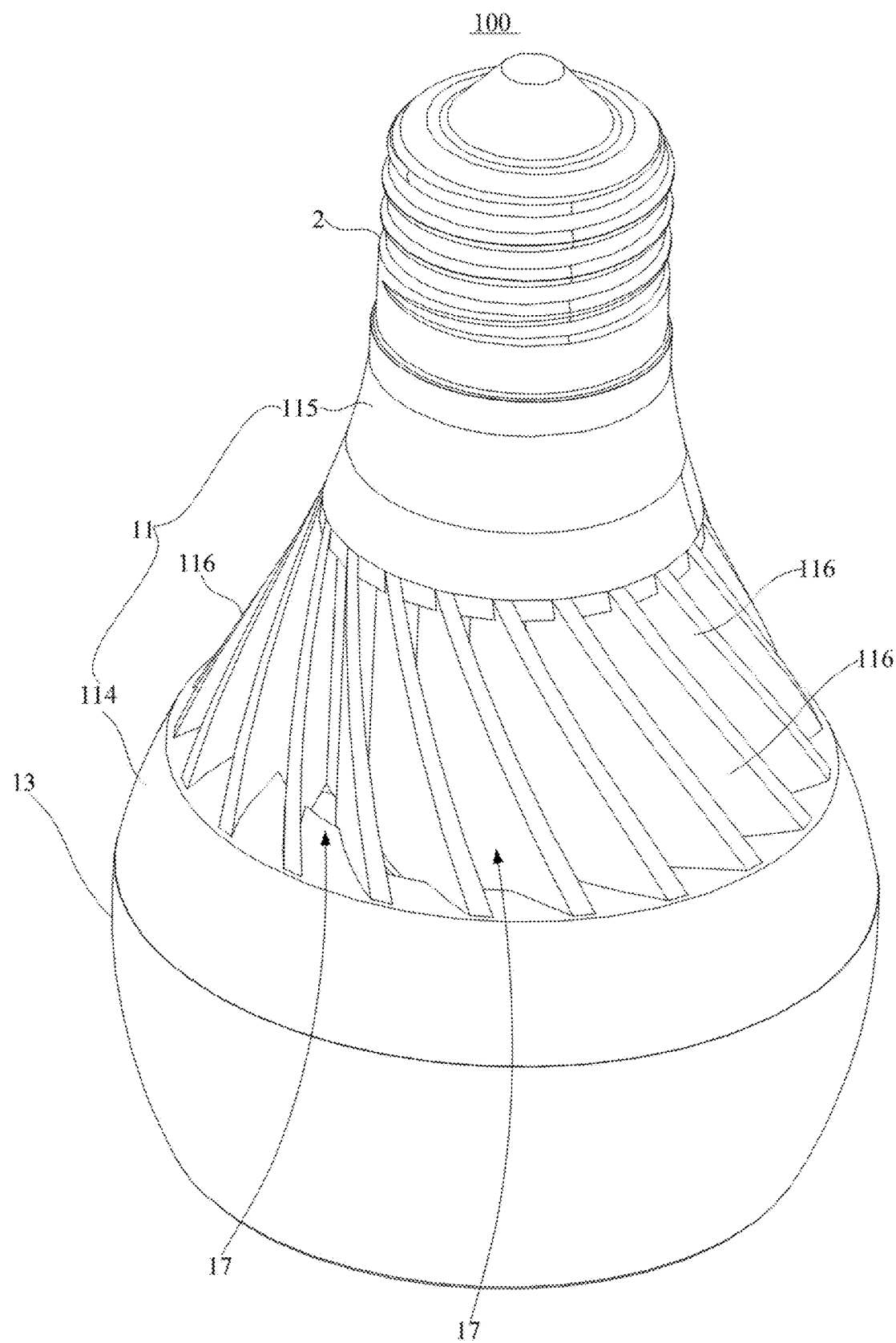
FIG. 1 is a schematic structural diagram of one embodiment of the present disclosure bulb lamp.
Figure 2:
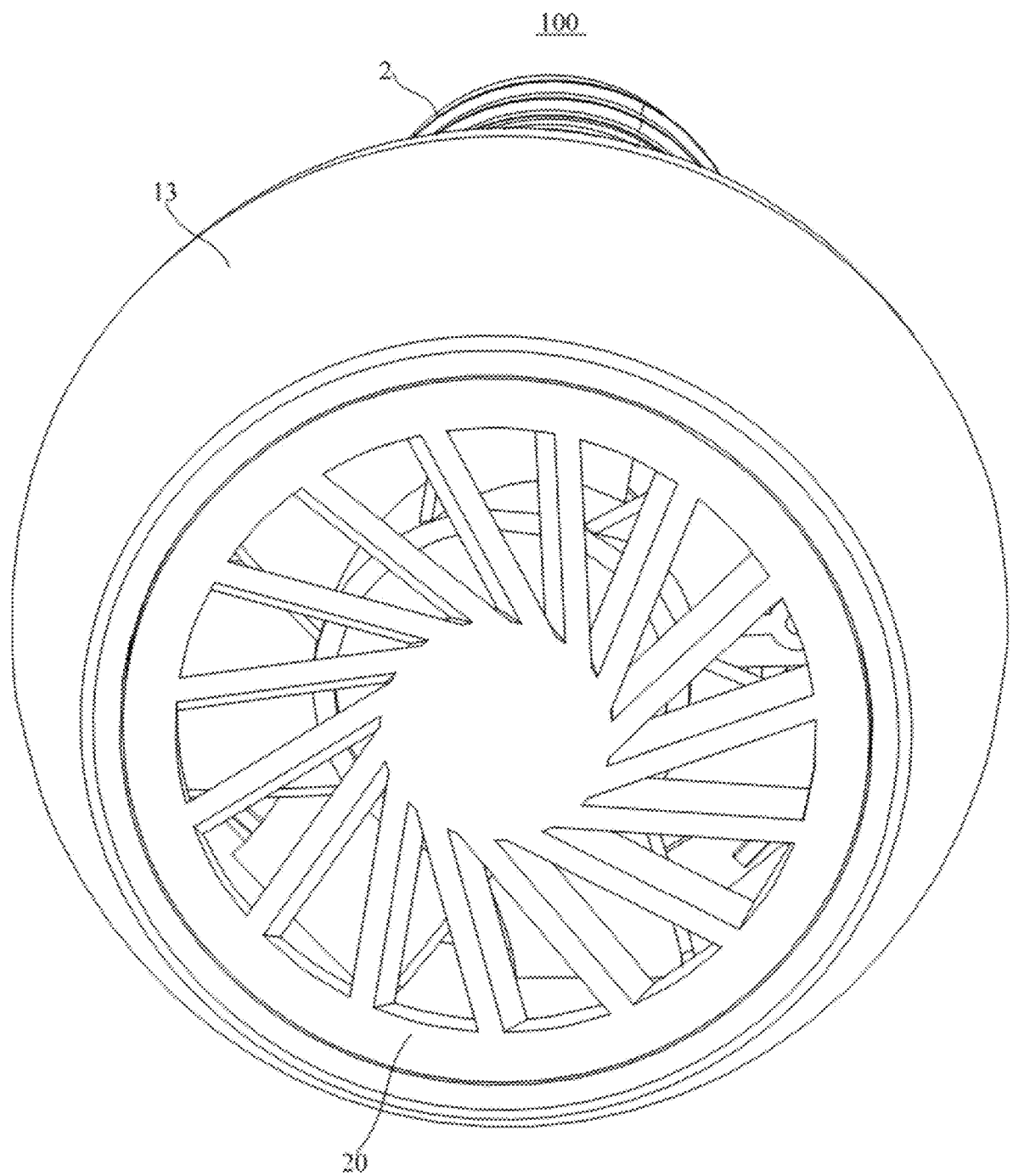
FIG. 2 is the schematic view of an alternative view of the bulb lamp of FIG. 1.

The shape, size, proportion or positional relationship of the component parts of the product shown in the drawings can be actual data of the embodiments and fall within the scope of protection of the present application.

DETAILED DESCRIPTION

In order that the objects, aspects and advantages of the present application will become more apparent, a more particular description of embodiments of the present application will be rendered by reference to the appended drawings. It should be understood that the particular embodiments described herein are illustrative only and are not restrictive.

With reference to FIGS. 1 to 5, the present disclosure proposes a bulb lamp 100, and in one embodiment of the present disclosure, the bulb lamp 100 comprises a lamp shell 11, a light-transmitting cover 13, a power panel 3, a lamp panel 4, at least one illumination module 5 and at least one sterilization module 6. The circumferential side of the lamp shell 11 extends internally into an annular first step 111, and a plurality of air inlets 17 are provided above the first step 111; the light-transmitting cover 13 is connected to the bottom ring side of the lamp shell 11, and encloses with the lamp shell 11 to form an accommodating cavity 15 in communication with the air inlet 17, and the bottom of the light-transmitting cover 13 is provided with at least one air outlet 19 in communication with the accommodating cavity 15; the power panel 3 is arranged in the accommodating cavity 15; the lamp panel 4 is provided in the accommodating cavity 15 and is lower than the first step 111, installation space 112 is formed between the lamp panel 4 and the first step 111, the lamp panel 4 is electrically connected to the power panel 3, and at least one circuit is provided on both the upper surface and the lower surface of the lamp panel 4; the illumination module 5 is provided on the lower surface of the lamp panel 4, and is electrically connected to the circuit on the lower surface of the lamp panel 4; the sterilization module 6 is disposed in the installation space 112 and electrically connected to the circuit on the upper surface of the lamp panel 4.

The combination of the lamp shell 11 and the light-transmitting cover 13 can be formed as main body structure of the bulb lamp 100, which can be successively arranged from top to bottom, and the two can enclose to form the accommodating cavity 15 so as to accommodate components such as the power panel 3, the lamp panel 4, the illumination module 5 and the sterilization module 6 of the bulb lamp 100. Here, the cross section of the lamp shell 11 may be arranged in descending manner in the direction from the bottom to the top, so that the upper end of the lamp shell 11 may have a relatively small volume to facilitate the sleeving and mounting of the lamp holder 2. The lamp holder 2 can be used for making electrical connection with the outside, i.e. providing at least one connection site, for example for making electrical connection with outside lamp-socket, so as to realize the external mounting of the bulb lamp 100. The light-transmitting cover 13 may be made of transparent material, so that the light emitted from the illumination module 5 is transmitted to the outside of the bulb lamp 100. In the direction from the top to the bottom, the cross section of the light-transmitting cover 13 may be arranged in descending manner, so that the air outlet 19 may be arranged at the position where the diameter of the light-transmitting cover 13 is relatively small, thereby facilitating the flow of air in convergent manner with large flow velocity and impact force. That is, the air flow under the bulb lamp 100 is better impacted, and the part of the air flow is driven to rise through the air inlet 17 on the lamp shell 11 and into the accommodating cavity 15 of the bulb lamp 100. The power panel 3 can be used to be electrically connected to the above-mentioned lamp holder 2 and the lamp panel 4, and convert the mains current transmitted from the lamp holder 2 into the constant voltage direct current to be sent to the lamp panel 4 and other electrical components in the bulb lamp 100, so as to ensure that the bulb lamp 100 can operate normally and stably. The lamp panel 4 may be adapted to be electrically connected to the power panel 3 and provide a mounting location for the illumination module 5 and the sterilization module 6. That is, by printing the electric circuit on both the upper surface and the lower surface of the lamp panel 4, the illumination module 5 and the sterilization module 6 can be electrically connected to the lamp panel 4 via the electric circuit on the lower surface and the electric circuit on the upper surface of the lamp panel 4, respectively, thereby realizing that the illumination module 5 and the sterilization module 6 share one lamp panel 4, thereby greatly improving the compactness of distribution between the two. In addition, the lamp panel 4 may also enclose the first step 11 on the inner side of the lamp shell 11 to form an installation space 112 for receiving the sterilization module 6 through the installation space 112. Wherein the first step 111 may comprise a first step surface and a second step surface which are connected, and the first step surface and the second step surface are both arranged circumferentially around the lamp shell 11, and the second step surface is located above the sterilization module 6 and is arranged at a spacing from the sterilization module 6, so as to form an installation space 112 between the lamp panel 4 and the first step 111, and at the same time, the structure of the first step 111 is relatively simple and the convenience of processing and shaping same is improved. The illumination module 5 can be used for performing light-emitting illumination after power-on, and can perform illumination on the outside of the bulb lamp 100 through the light-transmitting cover 13. The illumination module 5 can be a LED lamp bead, so that the illumination module 5 is directly mounted on the lamp panel 4. At the same time, since the LED lamp bead has the advantage of energy saving, it can also reduce the possibility of burn-out of the illumination module 5, and at the same time improve the environmental protection performance of the illumination module 5. Of course, it should be noted that the present application is not limited to this, and in other embodiments, the illumination module 5 may be small-sized bulb, so as to ensure that the illumination module 5 can achieve luminous illumination after being energized. The sterilization module 6 can be used to sterilize the air flow entering the accommodating cavity 15 so that the bulb lamp 100 can sterilize and purify the outside air. The sterilization module 6 can perform sterilization and disinfection by emitting ultraviolet rays.

Figure 3:
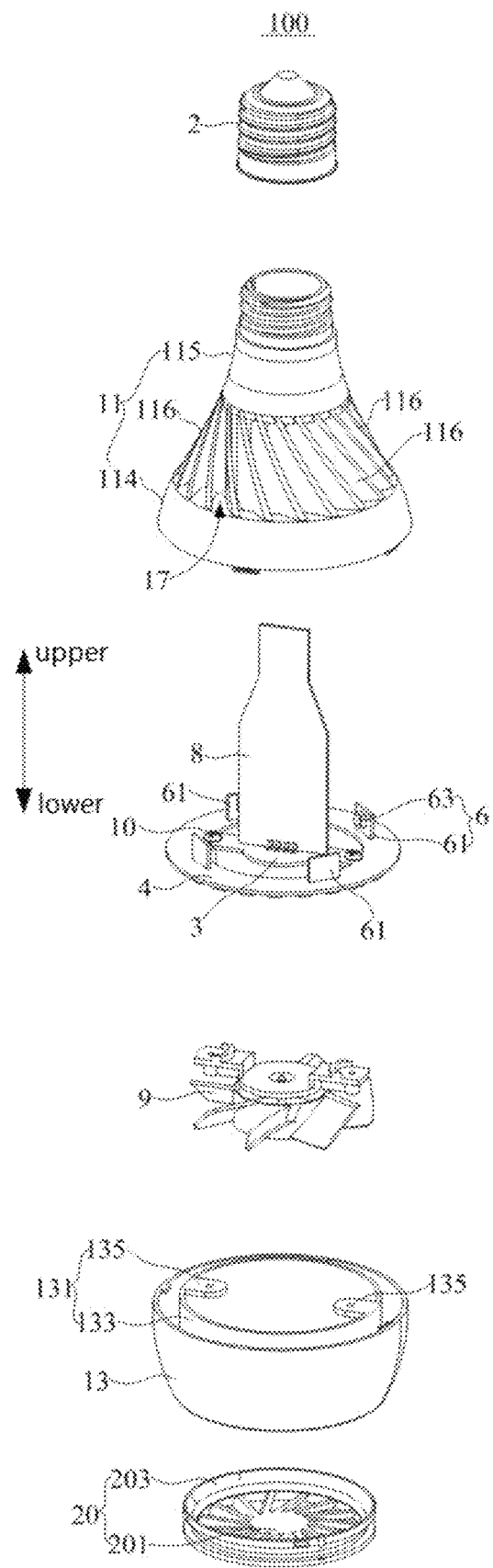
FIG. 3 is the schematic view showing the explosion structure of the bulb lamp of FIG. 1.
Figure 5:
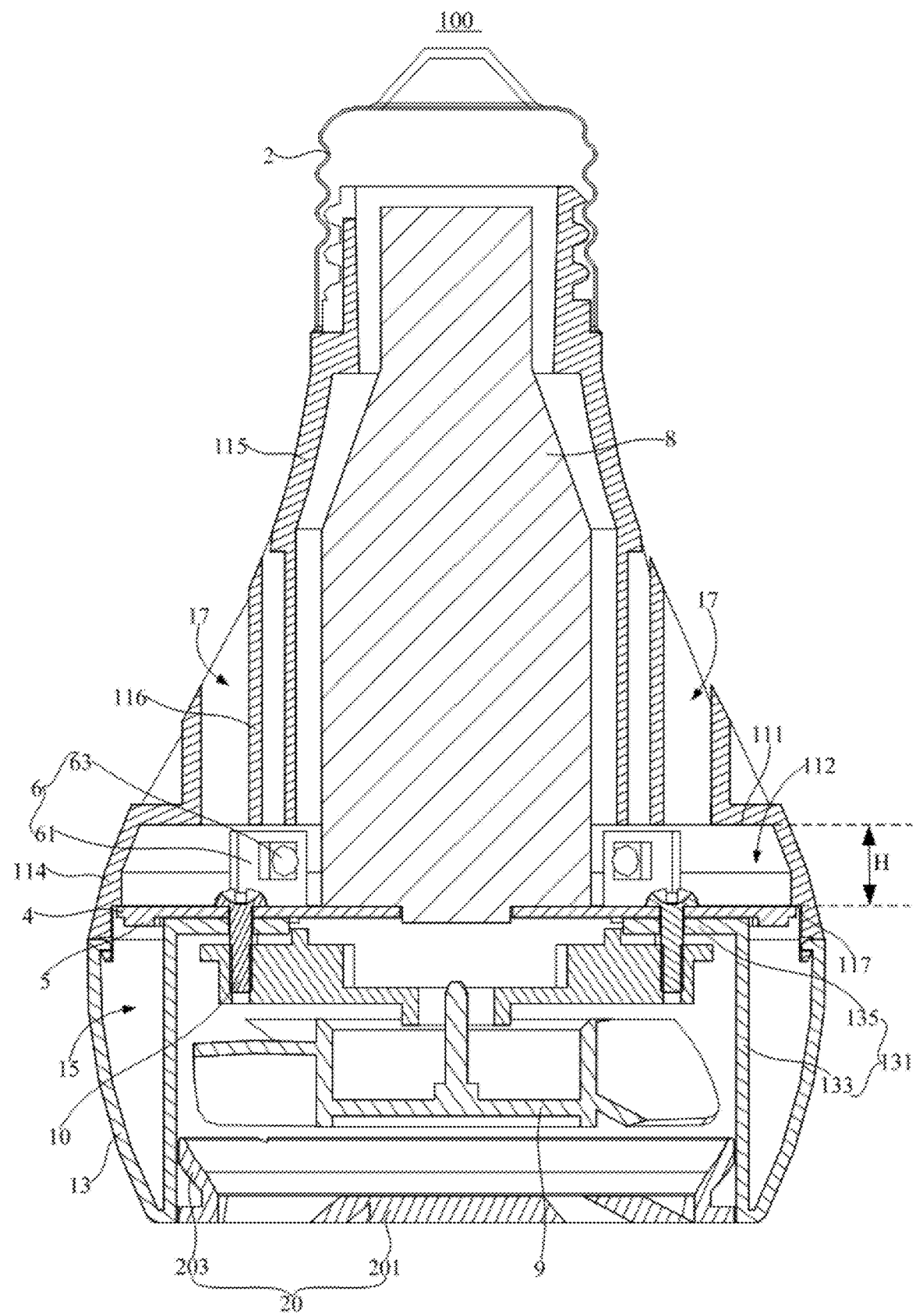
FIG. 5 is the schematic cross-sectional view of the bulb lamp of FIG. 1.

With reference to FIGS. 3 and 5 in combination, in one embodiment of the present disclosure, the light-transmitting cover 13 has a cylindrical structure with openings at both upper and lower ends, and the opening at the lower end of the light-transmitting cover 13 is formed as the air outlet 19; A support structure 131 is connected to the inner side of the lower end of the light-transmitting cover 13, the support structure 131 extends upwards, the lamp panel 4 is annular and is mounted on the support structure 131, at least two first jacks 45 are provided on the upper surface of the lamp panel 4, and the sterilization module 6 is inserted into the first jacks 45.

In the present embodiment, by providing the light-transmitting cover 13 as a cylindrical structure having openings at both upper and lower ends, the structure of the light-transmitting cover 13 can be made simple, and the air outlet 19 can be formed directly through the opening at the lower end of the light-transmitting cover 13, thereby improving the ease of manufacturing the light-transmitting cover 13. The lamp panel 4 is provided in the annular structure so that mounting positions can be given to the illumination module 5 and the sterilization module 6 in both circumferential directions, and thus the lighting and sterilizing functions of the bulb lamp 100 can be enhanced by mounting more illumination modules 5 and sterilization modules 6. The support structure 131 may then be arranged to provide the mounting location for mounting the lamp panel 4. The first jack 45 provided on the lamp panel 4 enables the sterilization module 6 to be inserted and fixed relatively simply, thereby facilitating the installation thereof. The sterilization module 6 may comprise at least one UV lamp panel 61 and at least one UV lamp bead 63, wherein the UV lamp panel 61 is inserted into the first jack 45 and electrically connected to the circuit on the upper surface of the lamp panel 4, the UV lamp bead 63 is provided on the UV lamp panel 61, and the light emitting direction of the UV lamp bead 63 faces the centre of the accommodating cavity 15. At this time, the UV lamp panel 61 can be conveniently used to be inserted into the first jack 45 so as to achieve quick installation of the sterilization module 6. Further, the cross-section of the light-transmitting cover 13 may be arranged in a decreasing manner in the direction from top to bottom, in which case on the one hand arrangement position may be provided for the support structure 131 in order to arrange the support structure 131. On the other hand, it is possible to make the caliber of the air outlet 19 relatively small, so that the air flow is discharged downwards with a better converging outflow.

With reference to FIGS. 3 to 7 in combination, in one embodiment of the present disclosure, the power panel 3 and the lamp panel 4 are located on the same plane and are spaced apart from the lamp panel 4, at least one circuit is provided on both the upper surface and the lower surface of the power panel 3, and the circuit on the upper surface of the power panel 3 is electrically connected to the lamp holder 2 and the circuit on the lower surface of the power panel 3; the bulb lamp 100 further comprises an electric connection plate 7, wherein the electric connection plate 7 is located on the same plane as the lamp panel 4 and the power panel 3, and two opposite ends of the electric connection plate 7 are respectively connected to the lamp panel 4 and the power panel 3, so that the circuit on the upper surface of the lamp panel 4 and the circuit on the lower surface are respectively electrically connected to the circuit on the upper surface and the lower surface of the power panel 3.

In this embodiment, the power panel 3 and the lamp panel 4 are arranged on the same plane, so that the power panel 3 and the lamp panel 4 can also be distributed very compactly to further reduce the occupation of space, thereby facilitating the arrangement of the power panel 3, the lamp panel 4, etc. in the limited space of the bulb lamp 100. In addition, when a circuit is provided on both the upper surface and the lower surface of the power panel 3, sufficient utilization of the upper and lower surfaces of the power panel 3 is achieved, so that the overall volume of the power panel 3 can be set relatively small, thereby further reducing the occupation of space. At the same time, this arrangement also facilitates the corresponding connection of the circuits on the upper surface and the lower surface of the power panel 3 with the circuits on the upper surface and the lower surface of the lamp panel 4 via the electric connection plate 7. Therefore, the upper and lower surfaces of the electric connection plate 7 may also be correspondingly printed with circuits for electrically connecting the circuits on the upper surface of the power panel 3 and the circuits on the upper surface of the lamp panel 4, and the circuits on the lower surface of the power panel 3 and the circuits on the lower surface of the lamp panel 4. Furthermore, the provision of the electric connection plate 7, in addition to serving as electrical connection, also serves as mechanical connection, so that the lamp panel 4 and the power panel 3 can be connected in one piece, thereby facilitating the subsequent mounting of this part of the structure at once. The electrical conduction between the circuit on the upper surface of the power panel 3 and the circuit on the lower surface thereof should be described as follows: two overrun holes penetrating the upper and lower surfaces of the power panel 3 are provided on the power panel 3, and then two lines are provided to realize the conduction of the circuit on the upper surface of the power panel 3 and the circuit on the lower surface of the power panel 3. In addition, in other embodiments, the power panel 3 and the lamp panel 4 may be spaced apart in the vertical direction. Alternatively, the lamp panel 4 is arranged horizontally, and the power panel 3 is arranged vertically, and this is not limited in the present application.

In one embodiment of the present disclosure, the power panel 3, the lamp panel 4 and the electric connection plate 7 are provided in an integrated structure.

In the present embodiment, by providing the power panel 3, the lamp panel 4, and the electric connection plate 7 as an integrated structure, the strength at the joint can be enhanced, thereby contributing to further increase the overall strength of the combination of the power panel 3, the lamp panel 4, and the electric connection plate 7. Moreover, this arrangement also makes it possible to manufacture the power panel 3, the lamp panel 4, and the electric connection plate 7 by integral molding, thereby contributing to the convenience of manufacturing thereof. In addition, the power panel 3, the lamp panel 4, and the electric connection plate 7 are integrally formed such that the installation of one of the power panel 3, the lamp panel 4, and the electric connection plate 7 is completed when one of the power panel 3, the lamp panel 4, and the electric connection plate 7 is installed on the support structure 131. Of course, it should be noted that the present application is not limited to this, and in other embodiments, the power panel 3, the lamp panel 4, and the electric connection plate 7 are provided in separate pieces, and subsequently fixed by means of adhesion, etc. is also possible.

Figure 6:
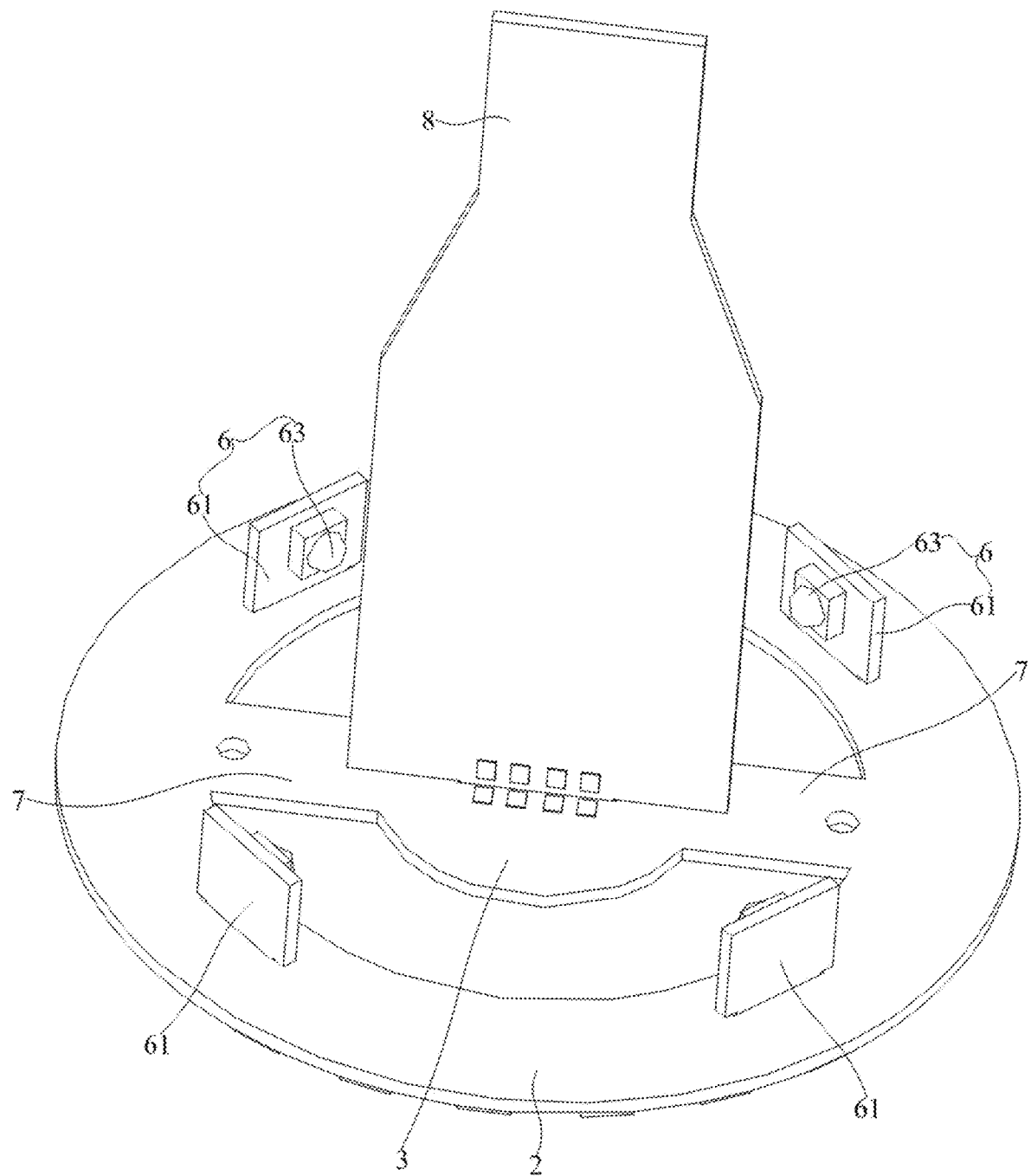
FIG. 6 is the partial schematic view of the bulb lamp of FIG. 3.
Figure 8:
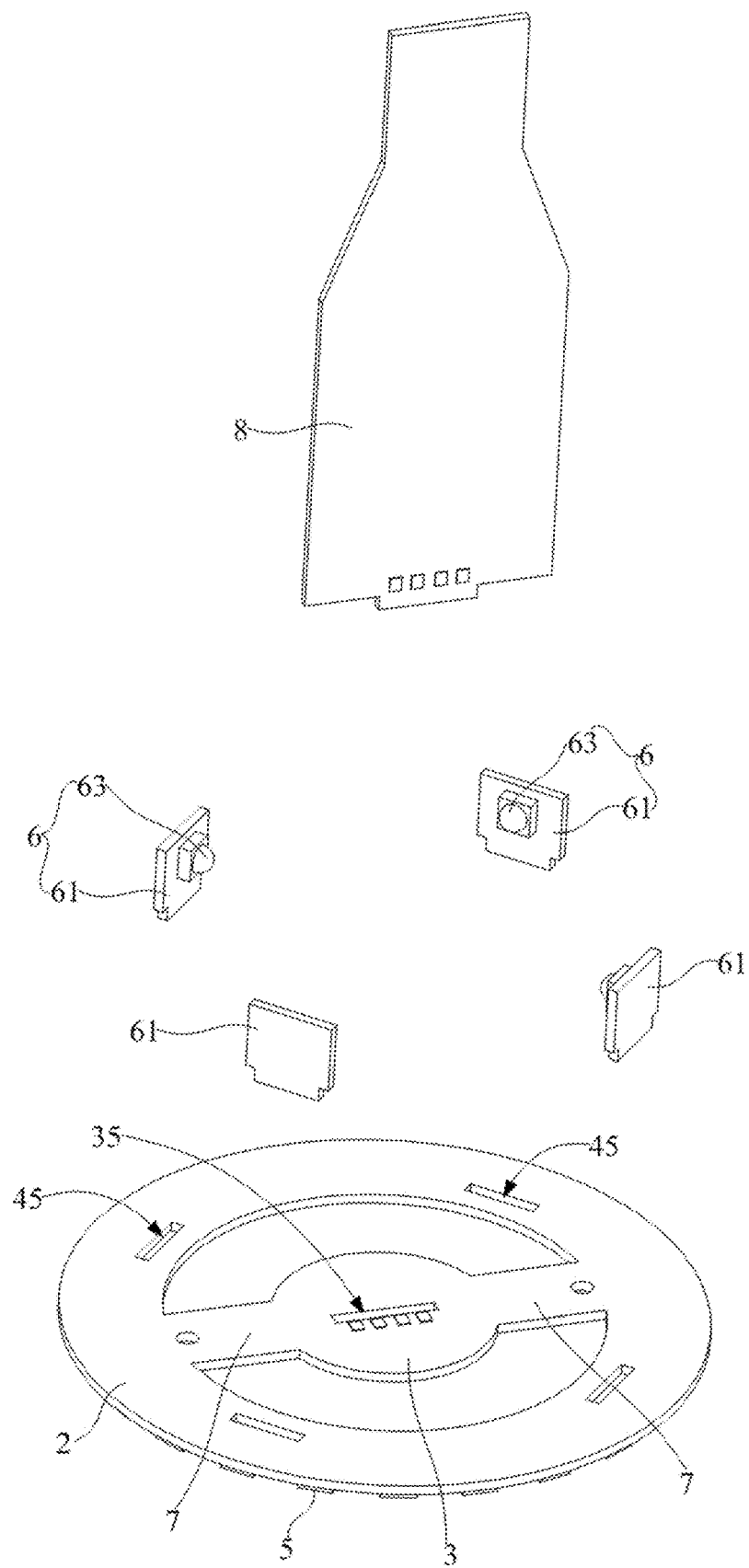
FIG. 8 is the exploded view of a portion of the bulb lamp of FIG. 3.

With reference to FIGS. 6 and 8, in one embodiment of the present disclosure, the power panel 3 is provided with the second jack 35, wherein the second jack 35 penetrates at least the upper surface of the power panel 3; the bulb lamp 100 further comprises at least one control panel 8, wherein the control panel 8 is provided in the accommodating cavity 15, and one end of the control panel 8 is electrically connected to the lamp holder 2, and the other end thereof is plugged into the second jack 35, and the control panel 8 is also electrically connected to at least one circuit on the upper surface of the power panel 3.

In the present embodiment, the electrical connection between the lamp holder 2 and the power panel 3 can be conveniently realized through the arrangement of the control panel 8. Furthermore, by limiting the installation of the control panel 8 via the second jack 35, the stability of the installation of the control panel 8 can be improved, so that the control panel 8 can normally play the role of electrical conduction after being stably in at least one preset installation position. The flow path of the current may specifically be: one is to flow from the lamp holder 2 to the control panel 8, then to the circuit on the upper surface of the power panel 3, and then to the circuit on the upper surface of the lamp panel 4 so as to supply power to the sterilization module 6; the second is to flow from the lamp holder 2 to the control panel 8, then to the circuit on the lower surface of the power panel 3, then to the circuit on the lower surface of the power panel 3, and then to the circuit on the lower surface of the lamp panel 4 so as to realize power supply to the illumination module 5. In addition, it should be noted that the power panel 3 may also be directly electrically connected to the lamp holder 2 via a wire body.

With reference to FIGS. 3 and 5 in combination, in one embodiment of the present disclosure, the support structure 131 comprises at least one support plate 133 and at least one fixing plate 135, wherein the support plate 133 is a cylindrical structure with openings at the upper and lower ends, and the lower end of the support plate 133 is connected to the light-transmitting cover 13 and is arranged around the air outlet 19; the fixing plate 135 is connected to the upper end of the support plate 133 and extends towards the inner side of the support plate 133, the lower surface of the lamp panel 4 and/or the electric connection plate 7 abuts against the fixing plate 135, and the electric connection plate 7 is connected to the fixing plate 135, and the illumination module 5 is located at the outer side of the support plate 133.

In the present embodiment, the support plate 133 has a cylindrical structure, so that the airflow in the accommodating cavity 15 can be better converged and guided to the air outlet 19, and the order of airflow flow can be improved. The fixing plate 135 preferably supports the lamp panel 4 and/or the electric connection plate 7, and also facilitates the direct mounting of the electric connection plate 7 to the fixing plate 135. The fixing plate 135 may abut only the lamp panel 4 or may abut only the electric connection plate 7. In order to improve the stability of the combined support and mounting of the lamp panel 4, the power panel 3 and the electric connection plate 7, it is preferable that part of the fixing plate 135 abuts against the lamp panel 4 and part of the fixing plate 135 abuts against the electric connection plate 7. In addition, in order to achieve the relatively simple structure, the number of the electric connection plates 7 and the support structures 131 can both be set as two, and one support structure 131 can be set corresponding to one electric connection plate 7, so that the stability of the combined support installation of the lamp panel 4, the power panel 3 and the electric connection plate 7 can be ensured, without the structure of the bulb lamp 100 being excessively complicated due to the large number of structures. Of course, it should be noted that the present application is not limited thereto, and in other embodiments, the support structure 133 may include only the support plate 133, in which case the electric connection plate 7 may be mounted directly to the support plate 133.

With reference to FIGS. 3 and 5 in combination, in one embodiment of the present disclosure, the bulb lamp 100 further comprises at least one fan module 9 and at least one locking screw 10, wherein the fan module 9 is provided on the inner side of the support plate 133 and is electrically connected to the circuit on the lower surface of the power panel 3; the locking screw 10 is sequentially inserted through the electric connection plate 7 and the fixing plate 135 and into the fan module 9, so that the electric connection plate 7, the fixing plate 135 and the fan module 9 are assembled and fixed.

In the present embodiment, the fan module 9 is mounted in the support plate 133 in a cylindrical structure, so that the compactness of the arrangement of the fan module 9 on the lamp body 1 can be improved. On the other hand, it is also possible by means of the fan module 9 to better drive the air flow in the direction from the inlet opening 17 into the accommodating cavity 15 and then out of the outlet opening 19. Since the lamp panel 4 and the power panel 3 are spaced apart, after entering the accommodating cavity 15 from the air inlet 17, the air flow can flow into the arc-shaped fixing plate 135 through the gap between the lamp panel 4 and the power panel 3, and then is discharged from the air outlet 19. Therefore, by arranging the lamp panel 4 and the power panel 3 at intervals as described above, the formation of the air-vent is also achieved, and there is no need to provide the air-vent through which the air flows on the lamp panel 4 or the power panel 3. In addition, since at least one circuit is provided on both the upper surface and the lower surface of the power panel 3, the fan module 9 provided below the power panel 3 can be electrically connected directly to the circuit on the lower surface of the power panel 3 very conveniently. By assembling the electric connection plate 7, the fixing plate 135 and the fan module 9 as a whole by passing through the locking screw 10, the fixing assembly of a plurality of components can be completed at once by directly passing through the locking screw 10 without connecting and fixing each other. At the same time, the screw connection also has the advantage of being simple and reliable, which contributes to a substantial increase in the ease of mounting the lamp panel 4, the power panel 3, the electric connection plate 7, the fixing plate 135 and the fan module 9.

Referring to FIG. 5, in one embodiment of the present disclosure, the fixing plate 135 is higher than the upper end of the light-transmitting cover 13.

In the present embodiment, since the fixing plate 135 is higher than the light-transmitting cover 13, the lamp panel 4 can be located in the lamp shell 11, and thus the sterilization module 6 provided on the upper surface of the lamp panel 4 is also located in the lamp shell 11, so that the sterilization module 6 can be better isolated and protected by the light-impermeable lamp shell 11, further reducing the possibility of the ultraviolet rays emitted from the sterilization module 6 being emitted to the outside.

With reference to FIGS. 3 and 5 in combination, in one embodiment of the present disclosure, the bulb lamp 100 further comprises at least one grid structure 20, wherein the grid structure 20 comprises at least one grid body 201 and at least one enclosing plate 203, the grid body 201 is arranged in the lower end of the support plate 133, the enclosing plate 203 is connected to the grid body 201 and is arranged around the periphery of the grid body 201, and in the direction from bottom to top, the cross section of the enclosing plate 203 is arranged in an increasing manner, so that the enclosing plate 203 is elastically clamped to the inner side wall of the support plate 133.

In this embodiment, the air outlet 19 can be covered on the one hand by the grid structure 20 to prevent foreign objects from easily entering the bulb lamp 100 from the air outlet 19 and damaging it. At the same time, the aesthetics of the overall appearance of the product can also be improved, thereby improving the competitiveness of subsequent products in the market. Furthermore, the grid structure 20 comprises at least one grid body 201 and at least one enclosing plate 203, wherein the grid body 201 can allow the passage of at least one air flow, and the enclosing plate 203 enables the air flow to be inwardly deformed, so that the grid structure 20 can be mounted in the support plate 133 by pressing from bottom to top, and is clamped and fixed by the enclosing plate 203 and the fixing plate 135 (namely, one of the enclosing plate 203 and the support plate 133 is provided with at least one snap, and the other thereof is provided with a clamping groove), thereby improving the convenience of mounting the grid structure 20.

Figure 4:
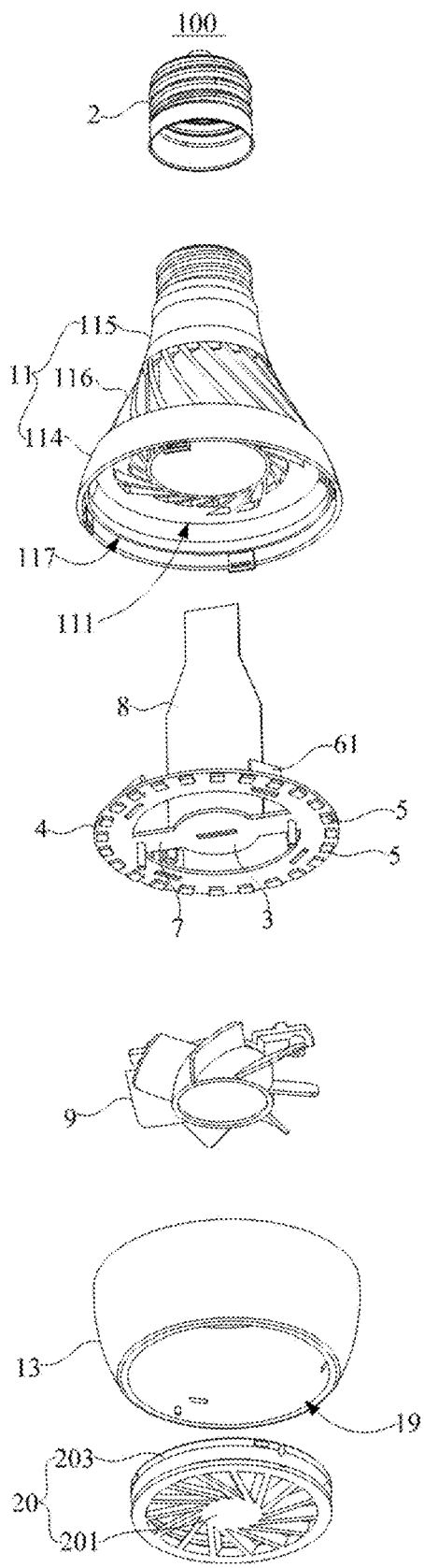
FIG. 4 is the schematic view of another perspective of the explosive structure of the bulb lamp of FIG. 1.
Figure 10:
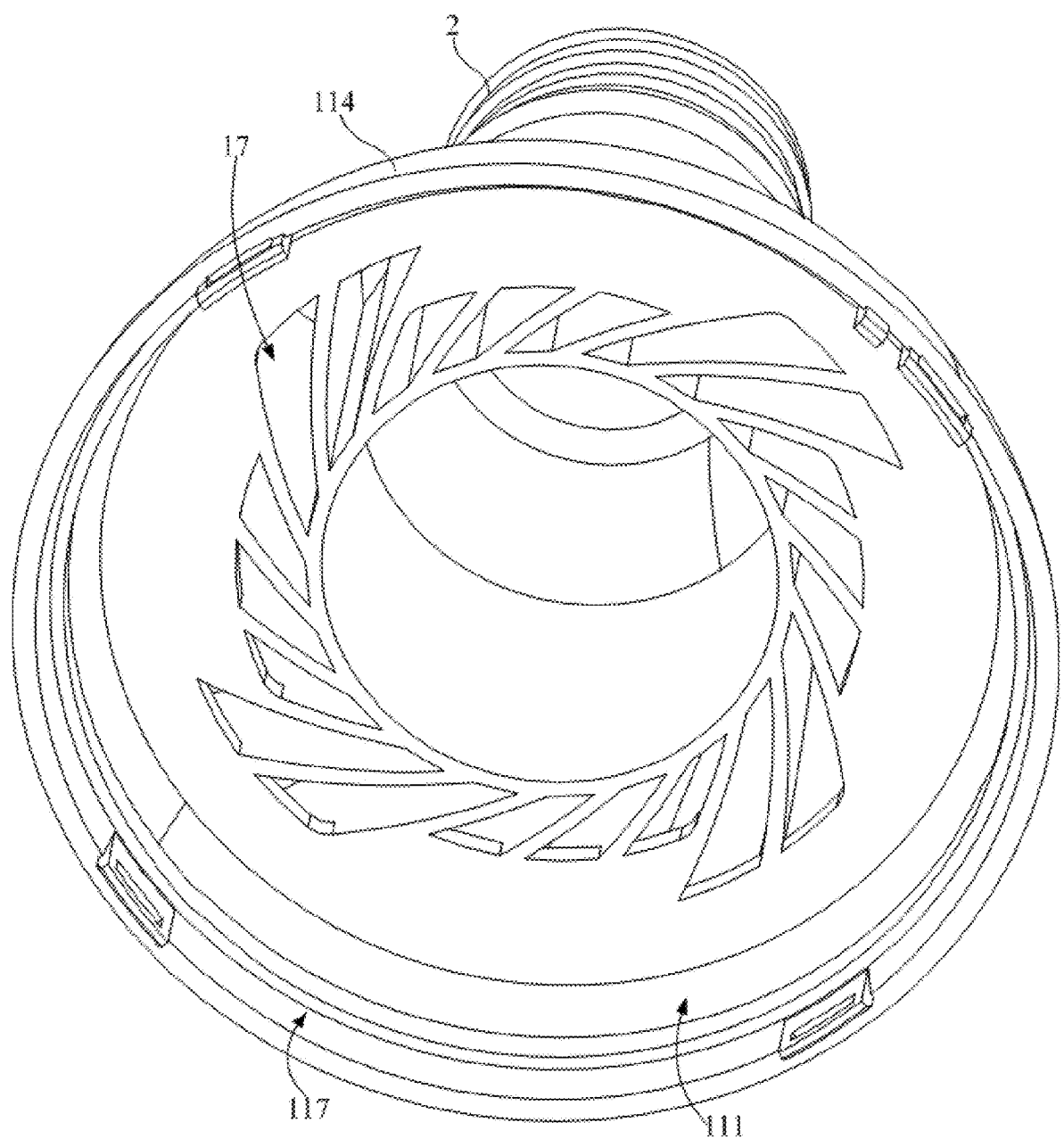
FIG. 10 is the schematic view of another view of the lamp shell of the bulb lamp of FIG. 1.

With reference to FIGS. 4, 5 and 10 in combination, in one embodiment of the present disclosure, the support plate 133, the fixing plate 135 and the light-transmitting cover 13 are provided in integral structure.

In this embodiment, by providing the support structure 131 and the light-transmitting cover 13 as the integral structure, it is possible to increase the strength of the two at the joint in order to increase the overall strength of the partial structure. The support structure 131 may also be transparent material, so as to improve the luminous and illuminating effect of the illumination module 5 on the outside.

Figure 7:
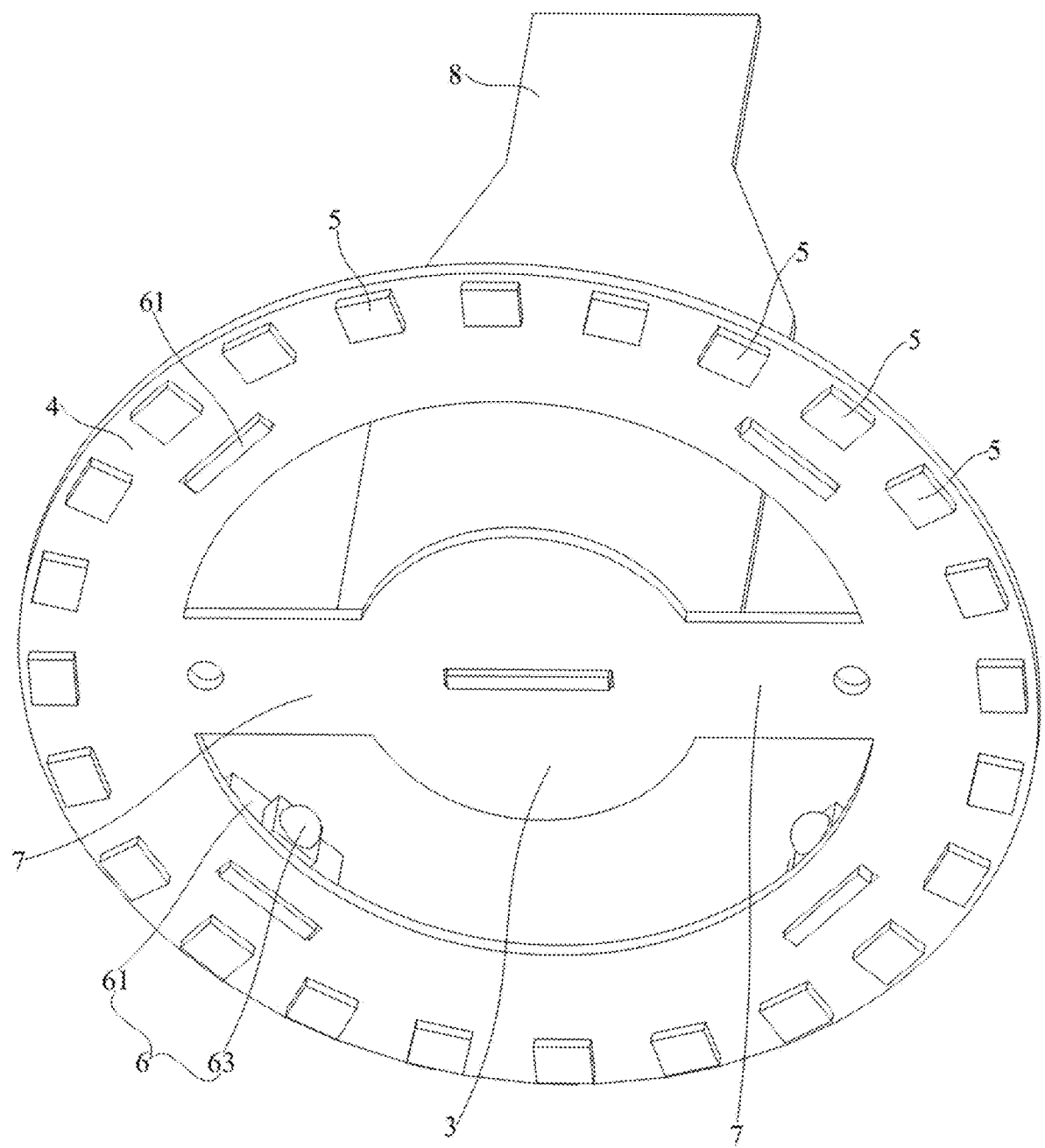
FIG. 7 is the schematic view of another perspective of the partial structure of the bulb lamp of FIG. 3.

With reference to FIGS. 6 and 7 in combination, in one embodiment of the present disclosure, the lamp panel 4 is in the shape of annular ring and is arranged around the power panel 3; the illumination module 5, the sterilization module 6 and the electric connection plate 7 are all provided with at least two; and the at least two illumination modules 5, the sterilization module 6 and the electric connection plate 7 are evenly spaced along the circumference of the lamp panel 4. The light-emitting directions of at least two illumination modules 5 are all vertically downwards, and the light-emitting directions of at least two sterilization modules 6 are all horizontally towards the centre of the accommodating cavity 15.

In the present embodiment, by surrounding the lamp panel 4 around the outside of the power panel 3, it is possible to make the distribution of the two more compact and to connect the lamp panel 4 and the power panel 3 by means of at least two electric connection plates 7 to improve the overall strength of the partial structure. In addition, the light-emitting direction of the illumination module 5 is arranged downwards, so that the illumination module 5 can be conveniently attached to the lower surface of the lamp panel 4 for mounting, so as to improve the convenience of mounting. Furthermore, the sterilization modules 6 emit light horizontally towards the centre of the accommodating cavity 15, so that the sterilization modules 6 all radiate horizontally inwards, and the possibility of the ultraviolet rays emitted by the sterilization modules 6 emitting outside can be better reduced. Here, it is to be noted that when the number of the electric connection plates 7 is at least two, circuits may be provided on only one of the upper and lower surfaces of the electric connection plates 7 to realize the circuit on the upper surface of the power panel 3 and the circuit on the upper surface of the lamp panel 4, and the circuit on the lower surface of the power panel 3 and the circuit on the lower surface of the lamp panel 4. In addition, the first step 111 is circumferentially arranged along the circumference of the lamp shell 11 so as to have a corresponding accommodating shielding effect on each of the plurality of sterilization modules 6 successively arranged along the circumference of the lamp panel 4.

Figure 9:
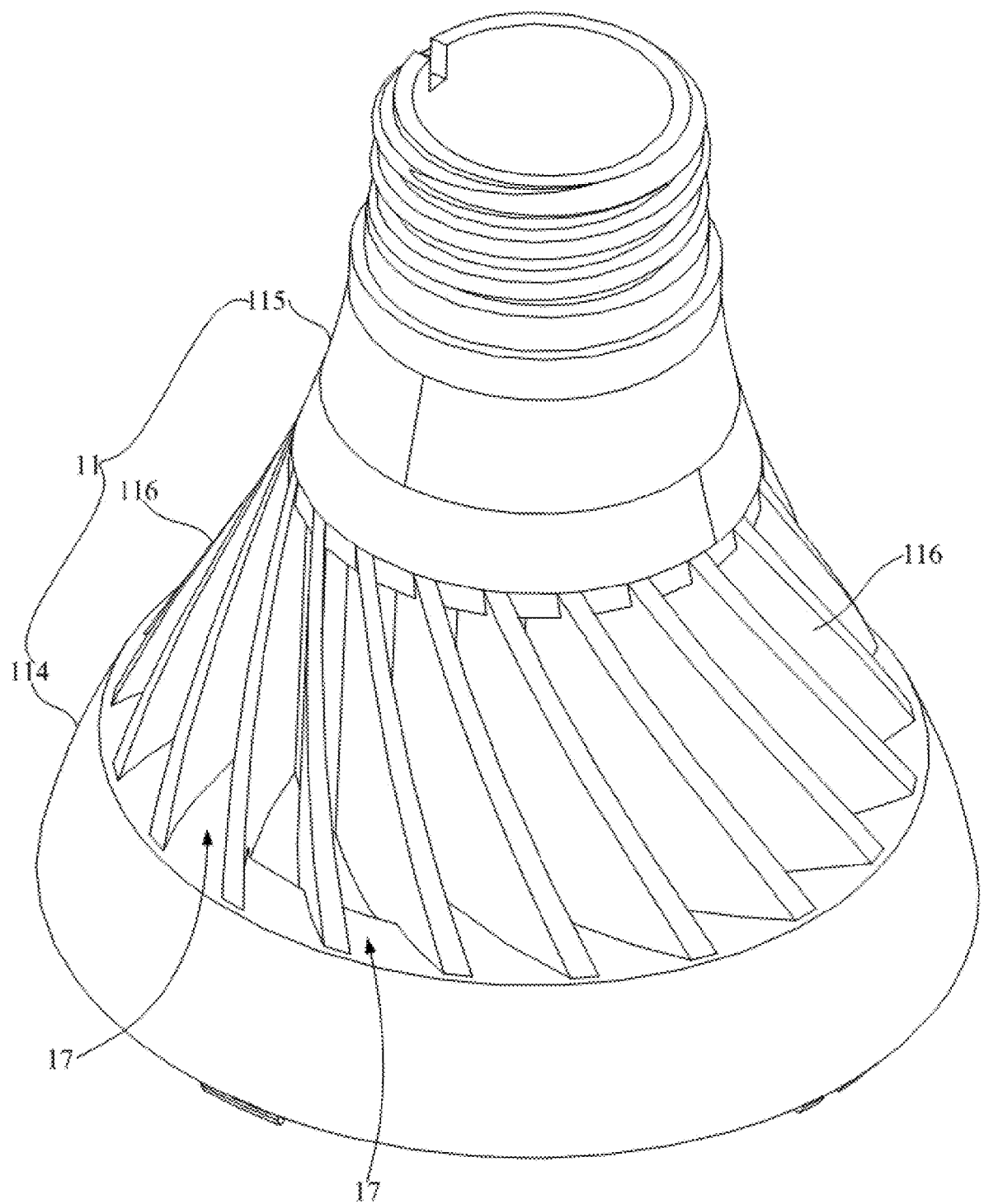
FIG. 9 is the schematic view showing a structure of a lamp shell of the bulb lamp of FIG. 1.

With reference to FIGS. 3, 5 and 9 in combination, in one embodiment of the present disclosure, the lamp shell 11 comprises a first shell section 114, a second shell section 115 and a plurality of guide vanes 116 from bottom to top, the lower end of the first shell section 114 is connected to the light-transmitting cover 13, and the first step 111 is formed on the inner side of the first shell section 114 away from the light-transmitting cover 13; the second shell section 115 is provided at one end of the first shell section 114 away from the light-transmitting cover 13, the cross section of the second shell section 115 is smaller than the cross section of the first shell section 114, and the lamp holder 2 is sheathed at one end of the second shell section 115 away from the first shell section 114; A plurality of guide vanes 116 are successively arranged at intervals along the circumferential direction of the lamp shell 11, and one end of each guide vane 116 is connected to the upper surface of the first step 111, and the other end thereof extends inward in arc shape and is connected to the outer side wall of the second shell section 115, and at least one air inlet 17 is formed between two adjacent guide vanes 116.

In this embodiment, the provision of the arc-shaped guide vanes 116 can guide the air flow spirally in the tangential direction into the accommodating cavity 15, and at this time, the flow rate of the air flow can be increased, thereby contributing to the improvement of the sterilization and purification efficiency of the air flow for the bulb lamp 100. Moreover, it is also possible to prevent a portion of the ultraviolet rays from being directly emitted to the outside due to the arc-shaped arrangement of the guide vane 116 even if the ultraviolet rays emitted from the sterilization module 6 are reflected into the air inlet 17.

With reference to FIGS. 4, 5 and 10, in one embodiment of the present disclosure, the second step 117 is further provided below the first step 111, and the outer periphery of the lamp panel 4 is limited below the second step 117.

In the present embodiment, the second step 117 allows the lamp panel 4 to be further abutted and limited, thereby further improving the stability of mounting the lamp panel 4. The second step 117 may be circumferentially arranged around the lamp shell 11 so as to abut against the circumferential direction of the lamp panel 4 in the circle to improve the limiting effect on the lamp panel 4. In addition, the second step 117 may comprise a third step surface and a fourth step surface which are connected, and may abut against the upper surface of the lamp panel 4 via the fourth step surface, or may further abut against the outer side surface of the lamp panel 4 via the third step surface, so as to improve the limiting effect thereon.

In one embodiment of the present disclosure, the light-transmitting cover 13 and the lamp shell 11 are clamped and fixed.

In the present embodiment, the light-transmitting cover 13 is fixed by snap-fitting (namely, one of the light-transmitting cover 13 and the lamp shell 11 is provided with a snap-fitting, and the other is provided with a snap-groove), so that the installation of the two is relatively simple, thereby facilitating the convenience of connecting the light-transmitting cover 13 and the lamp shell 11. Of course, in other embodiments, it is also possible that the light-transmitting cover 13 and the lamp shell 11 are connected by screws.

With reference to FIG. 5, in one embodiment of the present disclosure, the distance between the first step 111 and the upper surface of the lamp panel 4 is defined as H, satisfying the relationship: 4 mm≤H≤20 mm.

In the present embodiment, when the distance H between the first step 111 and the upper surface of the lamp panel 4 is less than 4 mm, the distance between the first step 111 and the lamp panel 4 is relatively small, which may cause inconvenience in mounting the sterilization module 6. However, when the distance H between the first step 111 and the upper surface of the lamp panel 4 is greater than 20 mm, the distance between the first step 111 and the lamp panel 4 is relatively large, which may make the overall volume of the lamp body 1 required to be set relatively large. Therefore, the distance H between the first step 111 and the upper surface of the lamp panel 4 is set to 4 mm to 20 mm in order to balance the convenience of installation of the sterilization module 6 and the compactness of the overall structure of the lamp body 1. Here, H is the distance between the second step surface of the first step 111 located above the lamp panel 4 and the upper surface of the lamp panel 4.

The above-mentioned description is merely a preferred embodiment of the present disclosure, and does not limit the scope of the patent of the present disclosure. Any equivalent structural transformation made by using the contents of the description and the drawings of the present disclosure under the inventive concept of the present disclosure, or direct/indirect application in other relevant technical fields, is included in the scope of the patent protection of the present disclosure.

What is claimed is:

1. A bulb lamp comprising:
   a lamp shell, wherein an annular first step extends inside a circumferential side of the lamp shell, and a plurality of air inlets are provided above the first step;
   a light-transmitting cover, wherein the light-transmitting cover is connected to a bottom ring side of the lamp shell and encloses with the lamp shell to form an accommodating cavity, the bottom of the light-transmitting cover is provided with at least one air outlet in communication with the accommodating cavity, and the accommodating cavity is in communication with the air inlet;
   a power panel, wherein the power panel is arranged in the accommodating cavity;
   a lamp panel, wherein the lamp panel is provided in the accommodating cavity and is arranged below the first step, an installation space is formed between the lamp panel and the first step, the lamp panel is electrically connected to the power panel, and an upper surface and a lower surface of the lamp panel are both provided with at least one circuit;
   at least one illumination module, wherein the illumination module is provided on the lower surface of the lamp panel and is electrically connected to the circuit on the lower surface of the lamp panel; and
   at least one sterilization module set in the installation space and electrically connected to the circuit of the upper surface of the lamp panel.

2. The bulb lamp as claimed in claim 1, wherein the light-transmitting cover has a cylindrical structure with openings at both upper and lower ends, a support structure is connected to an inner side of the lower end of the light-transmitting cover, and the support structure extends an upward direction; and
   the lamp panel is annular and mounted on the support structure, at least two first jacks are provided on the upper surface of the lamp panel, and the sterilization module is inserted into the first jacks.

3. The bulb lamp as claimed in claim 2, wherein the power panel and the lamp panel are located on the same plane and are spaced apart from the lamp panel, and both the upper surface and the lower surface of the power panel are provided with at least one circuit; and
   the bulb lamp further comprises at least one electric connection plate, opposite ends of the electric connection plate are connected to the lamp panel and the power panel, respectively, such that the circuit of the upper surface and the circuit of the lower surface of the lamp panel are electrically connected to the circuit of the upper surface and the circuit of the lower surface of the power panel, respectively.

4. The bulb lamp as claimed in claim 3, wherein the power panel is provided with at least one second jack, the second jack penetrating at least the upper surface of the power panel; the bulb lamp further comprises at least one lamp holder and at least one control panel, the lamp holder is sheathed on the upper end of the lamp shell, the control panel is arranged in the accommodating cavity, and one end of the control panel is electrically connected to the lamp holder, and the other end is plugged into the second jack, and the control panel is also electrically connected to the circuit on the upper surface of the power panel;
   and/or the power panel, the lamp panel and the electric connection plate are provided in an integrated structure;
   and/or a distance between the first step and the upper surface of the lamp panel is defined as H, satisfying the relationship: 4 mm≤H≤20 mm.

5. The bulb lamp as claimed in claim 3, wherein the support structure comprises:
   at least one support plate, the support plate having cylindrical structure with openings at both upper and lower ends, wherein the lower end of the support plate is connected to the light-transmitting cover and is arranged around the air outlet; and
   a fixing plate connected to the upper end of the support plate and extending towards the inner side of the support plate, the lower surface of the lamp panel and/or the electric connection plate abuts against the fixing plate, and the electric connection plate is connected to the fixing plate, and the illumination module is located at an outer side of the support plate.

6. The bulb lamp as claimed in claim 5, wherein the support plate, the fixing plate and the light-transmitting cover are provided in an integral structure;
   and/or the fixing plate is higher than the upper end of the light-transmitting cover;
   and/or the bulb lamp further comprises at least one fan module and at least one locking screw, wherein the fan module is provided on the inner side of the support plate and is electrically connected to the circuit on the lower surface of the power panel; the locking screw passes through the electric connection plate and the fixing plate successively and is inserted into the fan module so as to assemble and fix the electric connection plate, the fixing plate and the fan module;
   and/or the bulb lamp further comprises at least one grid structure, wherein the grid structure comprises at least one grid body and at least one enclosing plate, wherein the grid body is provided in the lower end of the support plate, and the enclosing plate is connected to the grid body and is circumferentially arranged along the periphery of the grid body; in the direction from bottom to top, the cross section of the enclosing plate is incrementally arranged so that the enclosing plate is snap-fitted to the inner side wall of the support plate.

7. The bulb lamp as claimed in claim 3, wherein that the lamp panel is shaped as an annular ring and is arranged around the power panel, at least two of the illumination module, the sterilization module and the electric connection plate are provided, and at least two of the illumination module, the sterilization module and the electric connection plate are evenly spaced along the circumference of the lamp panel; and the light-emitting directions of at least two of the illumination modules all face vertically downwards, and the light-emitting directions of at least two of the sterilization modules all face horizontally towards the center of the accommodating cavity.

8. The bulb lamp as claimed in claim 7, wherein the illumination module is at least one LED lamp bead;

and/or the sterilization module comprises at least one UV lamp panel and at least one UV lamp bead, wherein the UV lamp panel is inserted into the first jack and is electrically connected to the circuit on the upper surface of the lamp panel, the UV lamp bead is provided on the UV lamp panel, and the light output direction of the UV lamp bead faces the center of the accommodating cavity.

9. The bulb lamp as claimed in claim 1, wherein the lamp shell comprises, in a bottom to top arrangement:

a first shell section, the lower end of the first shell section connected to the light-transmitting cover, the first shell section being formed with the first step away from the inner side of the light-transmitting cover;

a second shell section provided at the end of the first shell section remote from the light-transmitting cover, and the cross section of the second shell section is smaller than the cross section of the first shell section; and a plurality of guide vanes, wherein the plurality of guide vanes are successively arranged at intervals along the circumferential direction of the lamp shell, and one end of each guide vane is connected to the upper surface of the first step, and another end thereof extends inward in an arc shape and is connected to the outer side wall of the second shell section, and the air inlet is formed between two adjacent guide vanes.

10. The bulb lamp as claimed in claim 9, wherein a second step is further provided below the first step, and the outer peripheral side of the lamp panel is limited below the second step;

and/or the light-transmitting cover and the lamp shell are clamped and fixed.

* * * * *